United States Patent
Celestini et al.

(10) Patent No.: US 10,807,962 B2
(45) Date of Patent: Oct. 20, 2020

(54) PROCESS FOR THE SYNTHESIS OF FIROCOXIB

(71) Applicant: COSMA S.P.A., Ciserano (IT)

(72) Inventors: Paolo Celestini, Romano di Lombardia (IT); Sergio Baretti, Boltiere (IT); Enrica Pizzatti, Poggiridenti (IT)

(73) Assignee: COSMA S.P.A., Ciserano (BG) (IT)

( * ) Notice: Subject to any disclaimer, the term of this patent is extended or adjusted under 35 U.S.C. 154(b) by 0 days.

(21) Appl. No.: 16/605,154

(22) PCT Filed: Apr. 14, 2017

(86) PCT No.: PCT/EP2017/059055
§ 371 (c)(1),
(2) Date: Oct. 15, 2019

(87) PCT Pub. No.: WO2018/188763
PCT Pub. Date: Oct. 18, 2018

(65) Prior Publication Data
US 2020/0102279 A1 Apr. 2, 2020

(51) Int. Cl.
*C07D 307/60* (2006.01)
(52) U.S. Cl.
CPC .................................. *C07D 307/60* (2013.01)
(58) Field of Classification Search
CPC .................................................. C07D 307/60
See application file for complete search history.

(56) References Cited

FOREIGN PATENT DOCUMENTS

| CN | 104803956 A | 7/2015 | |
|---|---|---|---|
| WO | 1997/014691 A1 | 4/1997 | |
| WO | WO 9737974 | * 10/1997 | ........... C07D 209/48 |

OTHER PUBLICATIONS

International Search Report and Written Opinion for corresponding Application No. PCT/EP2017/059055 (dated Nov. 28, 2017).
Leblanc et al., "SAR in the Alkoxy Lactone Series: The Discovery of DFP, a Potent and Orally Active Cox-2 Inhibitor," Bioorganic Med. Chem. Letts. 9(15):2207-2212 (1999).

* cited by examiner

*Primary Examiner* — Noble E Jarrell
(74) *Attorney, Agent, or Firm* — Troutman Pepper Hamilton Sanders LLP (Rochester)

(57) ABSTRACT

The present invention concerns a process for the preparation of firocoxib, i.e. 3-(cyclopropylmethoxy)-5,5-dimethyl-4-(4-methylsulfonylphenyl)-furan-2-one, comprising steps (a)-(g), wherein the process provides for step (d) of the reaction of a new intermediate, i.e. 2-methyl-1-[4-(methylsulfanyl)phenyl]-1-oxopropan-2-yl (acetyloxy)acetate (compound VII) in the same organic solvent of step (a) in the presence of a catalyst and a phase transfer catalyst solution in the same organic solvent with hydrogen peroxide.

13 Claims, 1 Drawing Sheet

Figure 1

PROCESS FOR THE SYNTHESIS OF FIROCOXIB

This application is a national stage application under 35 U.S.C. § 371 of PCT Application No. PCT/EP2017/059055, filed Apr. 14, 2017, which is hereby incorporated by reference in its entirety.

FIELD OF THE INVENTION

The present invention concerns a process for the preparation of firocoxib through the passage of a new intermediate.

STATE OF THE ART

Firocoxib, i.e. 3-(cyclopropylmethoxy)-5,5-dimethyl-4-(4-methylsulfonylphenyl)-furan-2-one, having formula is a non-steroidal antiflammatory drug of the class of (methylsulfonyl)-phenyl-2-(5h)-furanones Cox-2 inhibitors.

A family of (methylsulfonyl)-phenyl-2-(5h)-furanones is firstly described in WO97/14691 and the preparation of firocoxib is summarized in the scheme 1 as follows (as per example 1 (steps 1,2,3), example 109 (step 1), example 141 and example 148 of WO97/14691):

Scheme 1

The yield of the synthetic steps in each example is not included in the description. Furthermore the synthetic pathway includes the use of reagents not suitable for a plant production. In fact, the conversion of I into II includes the use of carbon tetrachloride, that belongs to the ozone-depleting chemicals class. The oxidation of II is performed using Oxone®, that is a mixture of three salts but just one of them is the oxidant species. Specifically, Oxone® corresponds to salt of peroxymonosulfuric acid. This potassium salt is a component of a triple salt with the formula $2KHSO_5 \cdot KHSO_4 \cdot K_2SO_4$. As above reported, the use of Oxone® needs large amount of reagent and solvents. Furthermore, the last step is performed using sodium hydride, an hazardous reagent, that generates hydrogen during the reaction. Finally compounds I, II and III are isolated during the synthetic route to give compound IV and a different solvent is used in each step.

It is evident that reagents and the high number of solvents are neither suitable and convenient for a plant production.

In the same document (WO97/14691) on page 82, under method K-1, the following transformation is described (Scheme 2):

Scheme 2

Intermediate VI was used for the synthesis of a class of (methylsulfonyl)-phenyl-2-(5h)-furanones, but neither proposed for firocoxib.

The inventors found out that the use of compound VI for the synthesis of Firocoxib according to the approaches described in WO97/14691 was not efficient, due to the formation of large amount of impurities. Additionally, compound VI was found not suitable for the preparation of compound III.

In CN104803956A, the above compound II reported in the scheme 1 was obtained from compound V as reported in paragraph [0008]. The use of sodium hydride for the alkylation of IV of WO97/14961 was overcome by the use of NaOH and of a phase transfer catalyst as reported in paragraph [0009], but the conversion of II into III was again performed with Oxone® as reported in paragraph [0007].

The object of the present invention is therefore to provide a process for the preparation of firocoxib that avoids the use of Oxone®, while being economically convenient and easily achievable for industrial scale production.

SUMMARY OF THE INVENTION

The object of the invention was achieved by a process for the preparation of 3-(cyclopropyl methoxy)-5,5-dimethyl-4-(4-methylsulfonylphenyl)-furan-2-one comprising the following steps:

(a) reacting thioanisole (1) with isobutyryl chloride (2) in the presence of a Lewis acid and an organic solvent, thus obtaining 2-methyl-1-[4-(methylsulfanyl)phenyl]propan-1-one (compound I)

(b) reacting 2-methyl-1-[4-(methylsulfanyl)phenyl]propan-1-one (compound I) with brominating agent in the same organic solvent of step (a), thus obtaining 2-bromo-2-methyl-1-[4-(methylsulfanyl)phenyl]propan-1-one (compound VI)

(c) reacting 2-bromo-2-methyl-1-[4-(methylsulfanyl)phenyl]propan-1-one (compound VI) with an aqueous solution of NaOH or KOH in the same organic solvent of step (a) and in the presence of a phase transfer catalyst, thus obtaining 2-hydroxy-2-methyl-1-[4-(methylsulfanyl)phenyl]propan-1-one (compound II)

(d) reacting 2-hydroxy-2-methyl-1-[4-(methylsulfanyl)phenyl]propan-1-one (compound II) with acetoxyacetyl chloride in the presence of the same organic solvent of step (a) and a basic compound, thus obtaining 2-methyl-1-[4-(methylsulfanyl)phenyl]-1-oxopropan-2-yl (acetyloxy)acetate (compound VII);

(e) reacting 2-methyl-1-[4-(methylsulfanyl)phenyl]-1-oxopropan-2-yl (acetyloxy)acetate (compound VII) in the same organic solvent of step (a) in the presence of a catalyst and a phase transfer catalyst solution in the same organic solvent with hydrogen peroxide, thus obtaining and separating 2-methyl-1-[4-(methylsulfonyl)phenyl]-1-oxopropan-2-yl (acetyloxy)acetate (compound VIII);

and

(g) reacting 3-hydroxy-5,5-dimethyl-4-[4-(methylsulfonyl)phenyl]furan-2(5H)-one (compound IV) with cyclopropylmethyl bromide in a suitable organic solvent, thus obtaining 3-(cyclopropylmethoxy)-5,5-dimethyl-4-(4-methylsulfonylphenyl)-furan-2-one

VII

IV

VIII (f) reacting a solution of 2-methyl-1-[4-(methylsulfonyl)phenyl]-1-oxopropan-2-yl (acetyloxy)acetate (compound VIII) with 1,8-diazabiciclo[5.4.0]undec-7-ene, thus is obtaining 3-hydroxy-5,5-dimethyl-4-[4-(methylsulfonyl)phenyl]furan-2(5H)-one (compound IV)

Firocoxib crude

The process of the invention thus allowed to obtain firocoxib, i.e. 3-(cyclopropylmethoxy)-5,5-dimethyl-4-(4-methylsulfonylphenyl)-furan-2-one through an original pathway, that avoids the use of Oxone® and is convenient for plant production. As a matter of fact, the transformation of Compound VII into Compound VIII was performed using hydrogen peroxide, thus avoiding the use of Oxone®. Furthermore the same organic solvent used in step (a) was used in the subsequent steps (b) to (e).

The process of the present invention allowed to obtain Compound VIII as the only species isolated prior to obtaining compound IV. No other separation are necessary with the process of the invention.

In another aspect the invention relates a new compound of formula (VII) which is an intermediate of the process of the invention allowing the advantageous step (e) of the process.

Without being bound to any theory, the inventors deem to have found an original synthetic pathway to Firocoxib by finding a new way of oxidation of the thiomethyl group of compound of Formula II, specifically by preparing the new intermediate compound of Formula VII. In the attempt to dispose of Oxone® oxidising compound, the inventors tried also to treat immediately compound of Formula II with hydrogen peroxide or peracetic acid, but this treatment gave formation of undesired byproducts.

Therefore the present invention achieved the object by providing also the new compound of Formula (VII), i.e. 2-methyl-1-[4-(methylsulfanyl)phenyl]-1-oxopropan-2-yl (acetyloxy)acetate.

In a preferred embodiment of the invention the process further includes step h) of crystallizing Firocoxib as white crystalline solid in methanol through a treatment with charcoal. The process of the invention allows to obtain an HPLC purity of Firocoxib of ≥99.7%.

DETAILED DESCRIPTION

The invention concerns a process for the preparation of 3-(cyclopropylmethoxy)-5,5-dimethyl-4-(4-methylsulfonylphenyl)-furan-2-one comprising the following steps:

(a) reacting thioanisole (1) with isobutyryl chloride (2) in the presence of a Lewis acid and an organic solvent, thus obtaining 2-methyl-1-[4-(methylsulfanyl)phenyl]propan-1-one (compound I)

(b) reacting 2-methyl-1-[4-(methylsulfanyl)phenyl]propan-1-one (compound I) with brominating agent in the same organic solvent of step (a), thus obtaining 2-bromo-2-methyl-1-[4-(methylsulfanyl)phenyl]propan-1-one (compound VI)

(c) reacting 2-bromo-2-methyl-1-[4-(methylsulfanyl)phenyl]propan-1-one (compound VI) with an aqueous solution of NaOH or KOH in the same organic solvent of step (a) and in the presence of a phase transfer catalyst, thus obtaining 2-hydroxy-2-methyl-1-[4-(methylsulfanyl)phenyl]propan-1-one (compound II)

(d) reacting 2-hydroxy-2-methyl-1-[4-(methylsulfanyl)phenyl]propan-1-one (compound II) with acetoxyacetyl chloride in the presence of the same organic solvent of step (a) and a basic compound, thus obtaining 2-methyl-1-[4-(methylsulfanyl)phenyl]-1-oxopropan-2-yl (acetyloxy)acetate (compound VII);

(e) reacting 2-methyl-1-[4-(methylsulfanyl)phenyl]-1-oxopropan-2-yl (acetyloxy)acetate (compound VII) in the same organic solvent of step (a) in the presence of a catalyst and a phase transfer catalyst solution in the same organic solvent with hydrogen peroxide, thus obtaining and separating 2-methyl-1-[4-(methylsulfonyl)phenyl]-1-oxopropan-2-yl (acetyloxy)acetate (compound VIII);

VII

VIII (f) reacting a solution of 2-methyl-1-[4-(methylsulfonyl)phenyl]-1-oxopropan-2-yl (acetyloxy)acetate (compound VIII) with 1,8-diazabiciclo[5.4.0]undec-7-ene, thus obtaining 3-hydroxy-5,5-dimethyl-4-[4-(methylsulfonyl)phenyl]furan-2(5H)-one (compound IV)

VIII

IV and (g) reacting 3-hydroxy-5,5-dimethyl-4-[4-(methylsulfonyl)phenyl]furan-2(5H)-one (compound IV) with cyclopropylmethyl bromide in a suitable organic solvent, thus obtaining 3-(cyclopropylmethoxy)-5,5-dimethyl-4-(4-methylsulfonylphenyl)-furan-2-one

IV

Firocoxib crude

Step (a) is the reaction of thioanisole (1) with isobutyryl chloride (2) in the presence of catalyst and an organic solvent, thus obtaining 2-methyl-1-[4-(methylsulfanyl)phenyl]propan-1-one (compound I).

Preferably the catalyst is aluminium trichloride and the organic solvent is dichloromethane. Dichlorometane is more preferably and advantageously the preferred organic solvent of steps (a)-(e). More preferably, operatively to a suspension of aluminium trichloride in dichloromethane firstly isobutyryl chloride is added dropwise and then thioanisole is added.

Step (b) is the reaction of 2-methyl-1-[4-(methylsulfanyl)phenyl]propan-1-one (compound I) with brominating agent in the same organic solvent of step (a), thus obtaining 2-bromo-2-methyl-1-[4-(methylsulfanyl)phenyl]propan-1-one (compound VI). Preferably the solution in dichloromethane of compound I was added with bromine molecule as brominating agent and the final organic solution after treatment with water is used in step (c).

Step (c) is the reaction of 2-bromo-2-methyl-1-[4-(methylsulfanyl)phenyl]propan-1-one (compound VI) with an aqueous solution of NaOH or KOH in the same organic solvent of step (a) and in the presence of a phase transfer catalyst, thus obtaining 2-hydroxy-2-methyl-1-[4-(methylsulfanyl)phenyl]propan-1-one (compound II). Preferably it is used an aqueous solution of NaOH, more preferably a 30% NaOH solution and the phase transfer catalyst was a solution of Aliquat® 336, more preferably in dichloromethane. Aliquat® 336 (Starks' catalyst) is a quaternary ammonium salt that contains a mixture of $C_8$ (octyl) and $C_{10}$ (decyl) chains with $C_8$ predominating and it is also known as N-Methyl-N,N,N-trioctylammonium chloride.

Step (d) is the reaction of 2-hydroxy-2-methyl-1-[4-(methylsulfanyl)phenyl]propan-1-one (compound II) with acetoxyacetyl chloride in the presence of the same organic solvent of step (a) and a basic compound, thus obtaining 2-methyl-1-[4-(methylsulfanyl)phenyl]-1-oxopropan-2-yl (acetyloxy)acetate (compound VII).

The organic solvent is preferably dichloromethane and is preferably added to the compound (II), obtained after distillation of the solution of compound (II) in dichloromethane of step (c). The basic compound is preferably pyridine.

The compound of formula (VII)

is a new compound and an intermediate of the process of the invention allowing the advantageous step (e) of the process. Therefore the present invention concerns also an intermediate compound of Formula (VII).

Step (e) is the reaction of 2-methyl-1-[4-(methylsulfanyl) phenyl]-1-oxopropan-2-yl (acetyloxy)acetate (compound VII) in the same organic solvent of step (a) in the presence of a catalyst and a phase transfer catalyst solution in the same organic solvent with hydrogen peroxide, thus obtaining and separating 2-methyl-1-[4-(methylsulfonyl)phenyl]-1-oxopropan-2-yl (acetyloxy)acetate (compound VIII).

Preferably the organic solvent is dichloromethane. More preferably the solution of compound (VII) in dichloromethane of step (d) is added with sodium tungstate dihydrate as a catalyst and with a solution of Aliquat® 336 as phase transfer catalyst in dichloromethane. Afterwards preferably a solution of 30% hydrogen peroxide is added dropwise. The compound (VIII) is separated after distillation of dichloromethane and it is preferably crystallized as powder, more preferably after the addition of toluene and isopropanol and subsequent drying.

Step (f) is the reaction of a solution of 2-methyl-1-[4-(methylsulfonyl)phenyl]-1-oxopropan-2-yl (acetyloxy)acetate (compound VIII) with 1,8-diazabiciclo[5.4.0]undec-7-ene, thus obtaining 3-hydroxy-5,5-dimethyl-4-[4-(methylsulfonyl)phenyl]furan-2(5H)-one (compound IV)

The solution of step (f) is preferably a solution in acetonitrile, and the reaction mixture is preferably heated and maintained at a temperature in the range from 60 to 80° C., more preferably at a temperature of about 72±2° C., still more preferably 72° C. After cooling compound (IV) is preferably filtered and used in the following step (g).

Step (g) is the reaction of 3-hydroxy-5,5-dimethyl-4-[4-(methylsulfonyl)phenyl]furan-2(5H)-one (compound IV) with cyclopropylmethyl bromide in a suitable organic solvent, thus obtaining 3-(cyclopropylmethoxy)-5,5-dimethyl-4-(4-methylsulfonylphenyl)-furan-2-one (firocoxib).

Preferably the suitable organic solvent is dimethylformamide and the reaction is more preferably carried out in the presence of a suitable metal base, more preferably $K_2CO_3$.

Preferably, the alkylation of compound IV is hence performed using cyclopropylmethyl bromide and potassium carbonate in dimethylformamide, thus avoiding the use of sodium hydride. The approach differs from the one described in CN104803956A, where compound IV is converted into Firocoxib by using cyclopropylmethyl bromide, NaOH and $Bu_4NBr$ in toluene.

In a preferred embodiment of the invention the process further includes step h) of crystallizing Firocoxib as white crystalline solid in methanol through a treatment with charcoal. The process of the invention allows to obtain an HPLC purity of Firocoxib of ≥99.7%.

Figure 1:
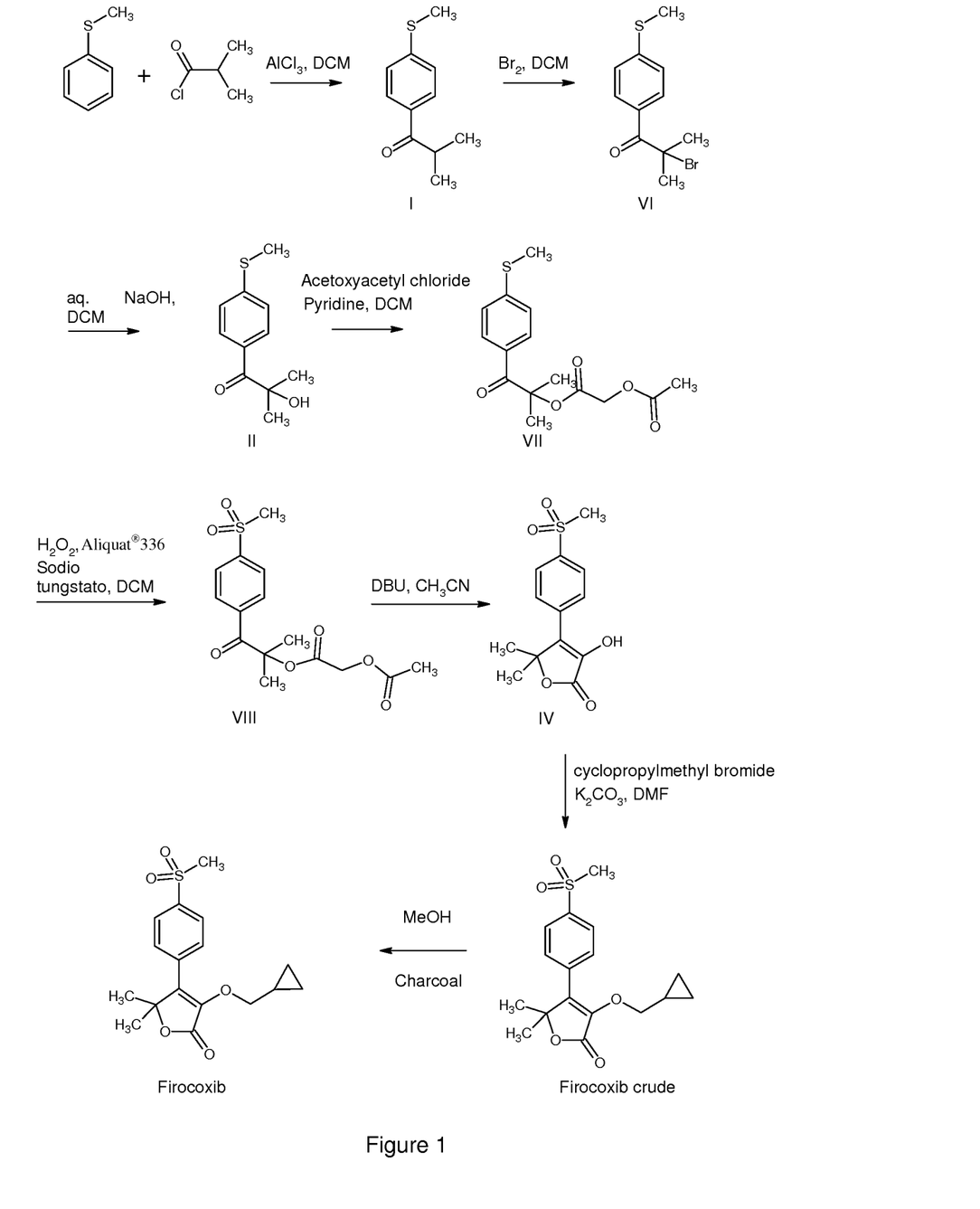
FIG. 1 is a detailed scheme with preferred ingredients of the process of the invention

The process as shown in FIG. 1 (Scheme 3) allowed to obtain Firocoxib in 61% overall yield, referring to the initial input of thioanisole. The HPLC purity of Firocoxib obtained according to such a process was ≥99.7%.

The invention will now be described with reference to some embodiments given by way of non-limiting example.

EXAMPLE 1

Step (a) Preparation of 2-methyl-1-[4-(methylsulfanyl)phenyl]propan-1-one (I)

To a suspension of Aluminium trichloride (76.73 g) in dichloromethane (650 ml) at 22±2° C., isobutyryl chloride (2) (61.30 g) was added dropwise, maintaining the temperature at 22±2° C. The mixture was held at 22±2° C. for 30 minutes, then thioanisole (1) (65.00 g) was added dropwise, maintaining the temperature at 22±2° C. and controlling the gas evolution. The reaction mixture was held at 22±2° C. for 3 hours, then it was slowly poured into a cold 5% HCl aqueous solution (342 g). The organic layer was separated and used as such in the subsequent step.

Step (b) Preparation of 2-bromo-2-methyl-1-[4-(methylsulfanyl)phenyl]propan-1-one (VI)

The solution of 2-methyl-1-[4-(methylsulfanyl)phenyl] propan-1-one (I) in dichloromethane obtained in Step (a) was heated to 30±2° C. Bromine (8.54 g) was added dropwise, the mixture was held at 30±2° C. for 1 hour to allow the bromination reaction to start. The mixture was cooled to 22±2° C., bromine (76.86 g) was added dropwise, controlling the gas evolution and maintaining the temperature at 22±2° C. Water (162 ml) was slowly added, maintaining the temperature below 30° C. After stirring for 15 minutes, the organic layer was separated and then washed with a solution of sodium sulfite (2.56 g) in water (81 ml). After stirring for 15 minutes, the organic layer was separated and used as such in the subsequent step.

Step (c) Preparation of 2-hydroxy-2-methyl-1-[4-(methylsulfanyl)phenyl]propan-1-one (II)

To the solution of 2-bromo-2-methyl-1-[4-(methylsulfanyl)phenyl]propan-1-one (VI) in dichloromethane obtained in Step (b) at 22±2° C., water (381 ml) was added, followed by aq. 30% NaOH (139.5 g) and a solution of Aliquat® 336 (5.79 g) in dichloromethane (9 ml). The mixture was stirred at 22±2° C. for 18 hours.

The organic layer was separated and then washed with water (75 ml). The organic layer was separated and used as such in the subsequent step.

Step (d) Preparation of 2-methyl-1-[4-(methylsulfanyl)phenyl]-1-oxopropan-2-yl (acetyloxy)acetate (VII)

The solution of 2-hydroxy-2-methyl-1-[4-(methylsulfanyl)phenyl]propan-1-one (II) in dichloromethane obtained in Step (c) was distilled under vacuum to residue, fresh dichloromethane (633 ml) was added followed by acetoxyacetyl chloride (92.82 g) and the temperature was adjusted to 40±2° C. Pyridine (53.78 g) was added over a period of 3 hours, then the mixture was held at 40±2° C. for 1 hour. The mixture was cooled to 22±2° C., water (300 ml) was added, the organic layer was separated and washed with water (75 ml). The organic layer was separated and used as such in the subsequent step.

Step (e) Preparation of 2-methyl-1-[4-(methylsulfonyl)phenyl]-1-oxopropan-2-yl (acetyloxy)acetate (VIII)

To the solution of 2-methyl-1-[4-(methylsulfanyl)phenyl]-1-oxopropan-2-yl (acetyloxy)acetate (VII) in dichloromethane obtained in Step (d) at 22±2° C., a solution of Sodium tungstate dihydrate (3.98 g) in water (36 ml) and a solution of Aliquat® 336 (5.81 g) in dichloromethane (6 ml) was added. A solution of 30% Hydrogen peroxide (136.31 g) was added dropwise in 2 hours, while maintaining the temperature at 22±2° C. After the addition the reaction mixture was held at 22±2° C. for 1 hour. The organic layer was separated, washed with a solution of 5% sodium sulfite (60 ml) and then with water (60 ml). Dichloromethane was removed by distillation and crystallization of the product was obtained after addition of toluene and isopropanol. The slurry was cooled to 0-5° C., held at 0-5° C. for 30 minutes and filtered, washing with isopropanol. The wet product was dried under vacuum at 50° C. to give 160.1 g of title compound as almost white powder.

Yield: 89% (referred to thioanisole).

Step (f) preparation of 3-hydroxy-5,5-dimethyl-4-[4-(methylsulfonyl)phenyl]furan-2(5H)-one (IV)

To a solution of 2-methyl-1-[4-(methylsulfonyl)phenyl]-1-oxopropan-2-yl (acetyloxy)acetate (VIII) (160.0 g) in acetonitrile (480 ml) at 22±2° C., 1,8-diazabiciclo[5.4.0]undec-7-ene (DBU) (188.57 g) was added and then the reaction mixture was heated to 72±2° C. and it was held at that temperature for 4 hours. The reaction mixture was cooled to 50±2° C. and water (240 ml) was added. The mixture was cooled to 22±2° C., 37% aq. HCl was added until pH 1-2, maintaining the temperature at 22±2° C., to give a suspension that was cooled to 0-5° C. The suspension was held at 0-5° C. for 1 hour, filtered and the product was washed with water (212 ml) to give 118.8 g of wet title compound as beige solid, that was used in the subsequent step without drying.

Step (g) Preparation of 3-(cyclopropylmethoxy)-5,5-dimethyl-4-[4-(methylsulfonyl)phenyl]furan-2(5H)-one (firocoxib)

To a mixture of the wet 3-hydroxy-5,5-dimethyl-4-[4-(methylsulfonyl)phenyl]furan-2(5H)-one (IV) obtained in Step (f) (118.8 g), dimethylformamide (725 ml) and $K_2CO_3$ (60.77 g) at 22±2° C., cyclopropylmethyl bromide (56.97 g) was added. The mixture was heated to 80±2° C. for 2 hours, then it was cooled to 50±2° C. Water (620 ml) was added over a period of at least 30 minutes, maintaining 50±2° C. The mixture was held at 50±2° C. for 30 minutes and the crystallization of the product occurred. Water (62 ml) was added over a period of at least 10 minutes. The suspension was cooled to 22±2° C. and held at that temperature for at least 4 hours. The suspension was filtered and the product was washed with water (370 ml) to give 150.0 g of wet crude Firocoxib as light beige solid. The wet crude Firocoxib was used in the subsequent step without drying.

Step h) Crystallization of 3-(cyclopropylmethoxy)-5,5-dimethyl-4-[4-(methylsulfonyl)phenyl]furan-2(5H)-one (Firocoxib)

A mixture of the wet crude 3-(cyclopropylmethoxy)-5,5-dimethyl-4-[4-(methylsulfonyl)phenyl]furan-2(5H)-one (Firocoxib) obtained in Step (g (150.0 g), methanol (777 ml) and charcoal (2.6 g) was heated to 60±2° C. Charcoal was filtered off on celite filter and the filter was washed with methanol (40 ml). Distillation was performed at ordinary pressure until removing 260 ml of solvent. The mixture was cooled to 50±2° C. and crystallization of the product occurred. The suspension was cooled to 0-5° C., held at that temperature for 1 hour, filtered and the product was washed with methanol (100 ml) to give wet Firocoxib (113.22 g) that was dried under vacuum at 60° C. to give 107.27 g of Firocoxib as white crystalline solid.

Overall yield 61.0% (referred to thioanisole).

HPLC purity: 99.9%

Example 2: Preparation and Characterization of the Intermediate 2-methyl-1-[4-(methylsulfanyl)phenyl]-1-oxopropan-2-yl (acetyloxy)acetate (VII)

The solution of 2-hydroxy-2-methyl-1-[4-(methylsulfanyl)phenyl]propan-1-one (II) in dichloromethane obtained in Step (c) was distilled under vacuum to residue, fresh dichloromethane (633 ml) was added followed by acetoxyacetyl chloride (92.82 g) and the temperature was adjusted to 40±2° C. Pyridine (53.78 g) was added over a period of 3 hours, then the mixture was held at 40±2° C. for 1 hour. The mixture was cooled to 22±2° C., water (300 ml) was added, the organic layer was separated and washed with water (75 ml). The organic layer was concentrated under vacuum to residue, isopropanol was added to promote the crystallization of the product.

The suspension was filtered and the product was washed with isopropanol and dried under vacuum to give 111.6 g of title compound as off white solid.

Proton NMR spectra were recorded on a Bruker Avance 400 spectrometer operating at 400.13 MHz. Proton chemical shifts are reported in ppm (d) with the solvent reference relative to tetramethylsilane (TMS) employed as the internal standard (dmso-d6, d=2.50 ppm and D2O, d=4.80 ppm). The following abbreviations are used to describe spin multiplicity: s=singlet, d=doublet, t=triplet, q=quartet, m=multiplet, bs=broad signal, dd=doubletdoublet.

$^1$H-NMR (CDCl$_3$, 400 MHz): 1.66 (s, 6H, (CH$_3$)$_2$O); 2.02 (s, 3H, CH$_3$CO); 2.44 (s, 3H, CH$_3$S); 4.43 (s, 2H, CH$_2$); 7.16 (d, 2H, Aromatics, J=8.5 Hz); 7.84 (d, 2H, Aromatics, J=8.5 Hz).

The invention claimed is:

1. A process for the preparation of 3-(cyclopropylmethoxy)-5,5-dimethyl-4-(4-methylsulfonylphenyl)-furan-2-one comprising the following steps:

(a) reacting thioanisole (1) with isobutyryl chloride (2) in the presence of a catalyst and an organic solvent, thus obtaining 2-methyl-1-[4-(methylsulfanyl)phenyl]propan-1-one (compound I)

(b) reacting 2-methyl-1-[4-(methyl sulfanyl)phenyl]propan-1-one (compound I) with brominating agent in the same organic solvent of step (a), thus obtaining 2-bromo-2-methyl-1-[4-(methylsulfanyl)propan-1-one (compound VI)

(c) reacting 2-bromo-2-methyl-1-[4-(methylsulfanyl)phenyl]propan-1-one (compound VI) with an aqueous solution of NaOH or KOH in the same organic solvent of step (a) and in the presence of a phase transfer catalyst, thus obtaining 2-hydroxy-2-methyl-1-[4-(methylsulfanyl)phenyl]propan-1-one (compound II)

(d) reacting 2-hydroxy-2-methyl-1-[4-(methylsulfanyl)phenyl]propan-1-one (compound II) with acetoxyacetyl chloride in the presence of the same organic solvent of step (a) and a basic compound, thus obtaining 2-methyl-1-[4-(methylsulfanyl)phenyl]-1-oxopropan-2-yl (acetyloxy)acetate (compound VII);

(e) reacting 2-methyl-1-[4-(methyl sulfanyl)phenyl]-1-oxopropan-2-yl (acetyloxy)acetate (compound VII) in the same organic solvent of step (a) in the presence of a catalyst and a phase transfer catalyst solution in the same organic solvent with hydrogen peroxide, thus obtaining and separating 2-methyl-1-[4-(methylsulfonyl)phenyl]-1-oxopropan-2-yl (acetyloxy)acetate (compound VIII);

(f) reacting a solution of 2-methyl-1-[4-(methylsulfonyl)phenyl]-1-oxopropan-2-yl (acetyloxy)acetate (compound VIII) with 1,8-diazabiciclo[5.4.0]undec-7-ene, thus obtaining 3-hydroxy-5,5-dimethyl-4-[4-(methylsulfonyl)phenyl]furan-2(5H)-one (compound IV)

VIII

IV and (g) reacting 3-hydroxy-5,5-dimethyl-4-[4-(methylsulfonyl)phenyl]furan-2(5H)-one (compound IV) with cyclopropylmethyl bromide in a suitable organic solvent, thus obtaining 3-(cyclopropylmethoxy)-5,5-dimethyl-4-(4-methylsulfonylphenyl)-furan-2-one

IV

Firocoxib crude

2. The process according to claim 1, wherein in step (a) the catalyst is aluminium trichloride and the organic solvent is dichloromethane.

3. The process according to claim 1, wherein dichloromethane is the organic solvent of steps (a)-(e).

4. The process according to claim 1, wherein the brominating agent of step (b) is bromine molecule.

5. The process according to claim 1, wherein in step (c) a solution of NaOH is used and the phase transfer catalyst is a solution of N-methyl-N,N,N-trioctylammonium chloride.

6. The process according to claim 1, wherein step (d) is carried out in the presence of pyridine.

7. The process according to claim 1, wherein in step (e) sodium tungstate dihydrate is used as catalyst and a solution of N-methyl-N,N,N-trioctylammonium chloride in dichloromethane is used as phase transfer catalyst.

8. The process according to claim 1, wherein in step (f) the solution of 2-methyl-1-[4-(methyl sulfonyl)phenyl]-1-oxopropan-2-yl (acetyloxy)acetate (compound VIII) is a solution in acetonitrile.

9. The process according to claim 1, wherein the suitable organic solvent is dimethylformamide and the reaction of step (g) is carried out in the presence of a metal base.

10. The process according to claim 1, wherein the process further comprises step h) of crystallizing Firocoxib in methanol through a treatment with charcoal.

11. The process according to claim 1, wherein Firocoxib is obtained with a HPLC purity of ≥99.7%.

12. An intermediate compound of Formula 2-methyl-1-[4-(methylsulfanyl)phenyl]-1-oxopropan-2-yl (acetyloxy)acetate (compound VII)

VII

13. The process according to claim 9, wherein the metal base of step (g) is K₂CO₃.

* * * * *